United States Patent [19]

Hood, III

[11] 4,259,961

[45] Apr. 7, 1981

[54] COOLING PAD

[76] Inventor: Andrew G. Hood, III, 34877 Forest Estates Rd., Evergreen, Colo. 80489

[21] Appl. No.: 6,180

[22] Filed: Jan. 24, 1979

[51] Int. Cl.³ .......................... A61F 7/00; A61F 7/12
[52] U.S. Cl. .................................. 128/400; 128/401; 128/402
[58] Field of Search .............. 128/399, 400, 402, 401, 128/DIG. 20, 87

[56] References Cited

U.S. PATENT DOCUMENTS

| | | | |
|---|---|---|---|
| 2,250,325 | 7/1941 | Barnes .............................. | 128/400 X |
| 3,091,242 | 5/1963 | Johnson et al. ...................... | 128/402 |
| 3,738,372 | 6/1973 | Shioshvili ............................. | 128/400 |
| 3,745,998 | 7/1973 | Rose ...................................... | 128/87 |
| 3,757,366 | 9/1973 | Sacher ................................... | 128/400 |
| 3,888,259 | 6/1975 | Miley .................................... | 128/400 |
| 4,154,245 | 5/1979 | Daily .................................... | 128/402 |

*Primary Examiner*—Robert W. Michell
*Assistant Examiner*—C. W. Shedd

[57] ABSTRACT

A cooling pad for maintaining low organ metabolism has a pair of flexible walls sealed together at their edges except at an inlet and an outlet, which are disposed away from each other, the walls enclosing a flexible and porous foam filler which separates them.

8 Claims, 5 Drawing Figures

U.S. Patent     Apr. 7, 1981     4,259,961
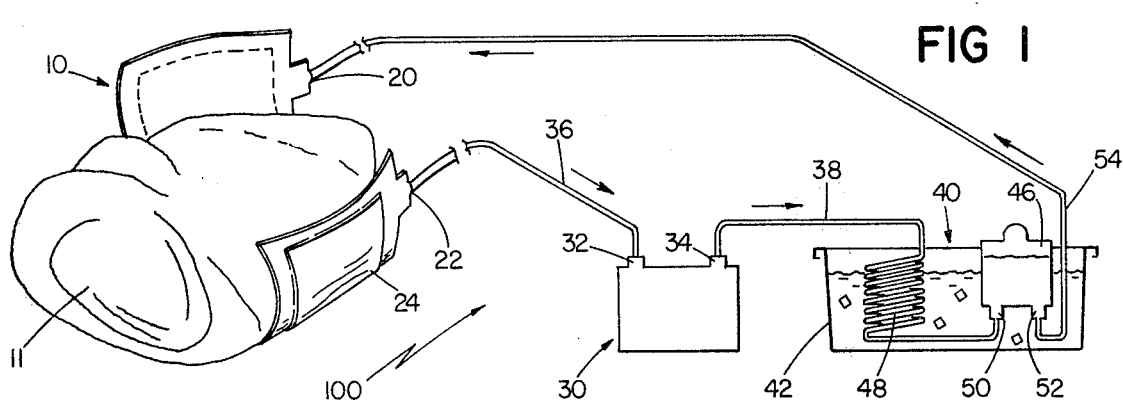
FIG 1
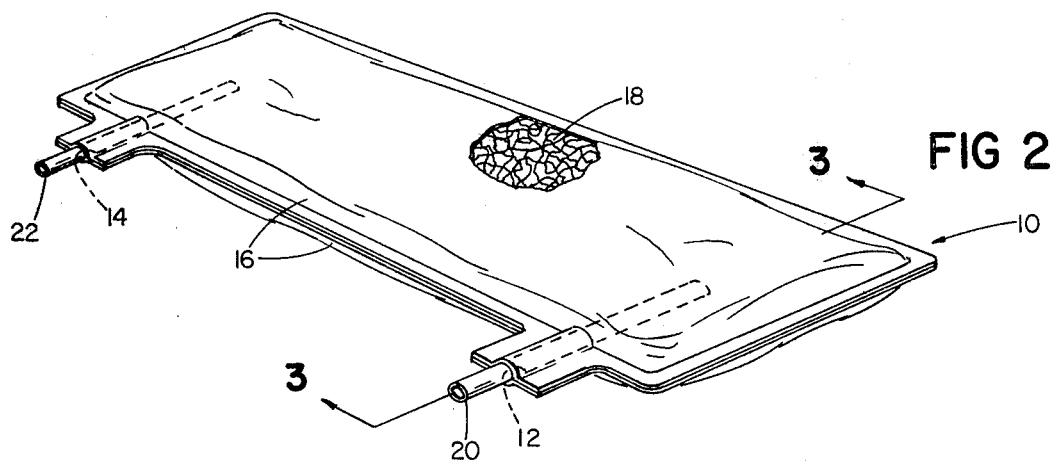
FIG 2
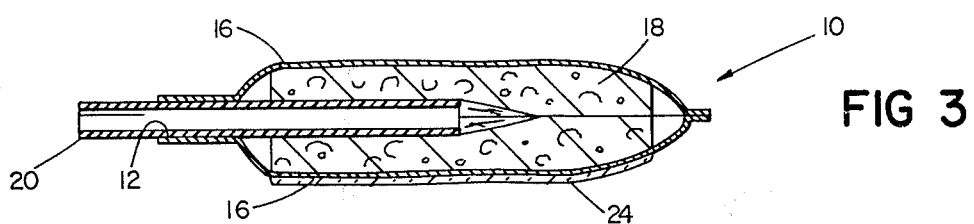
FIG 3
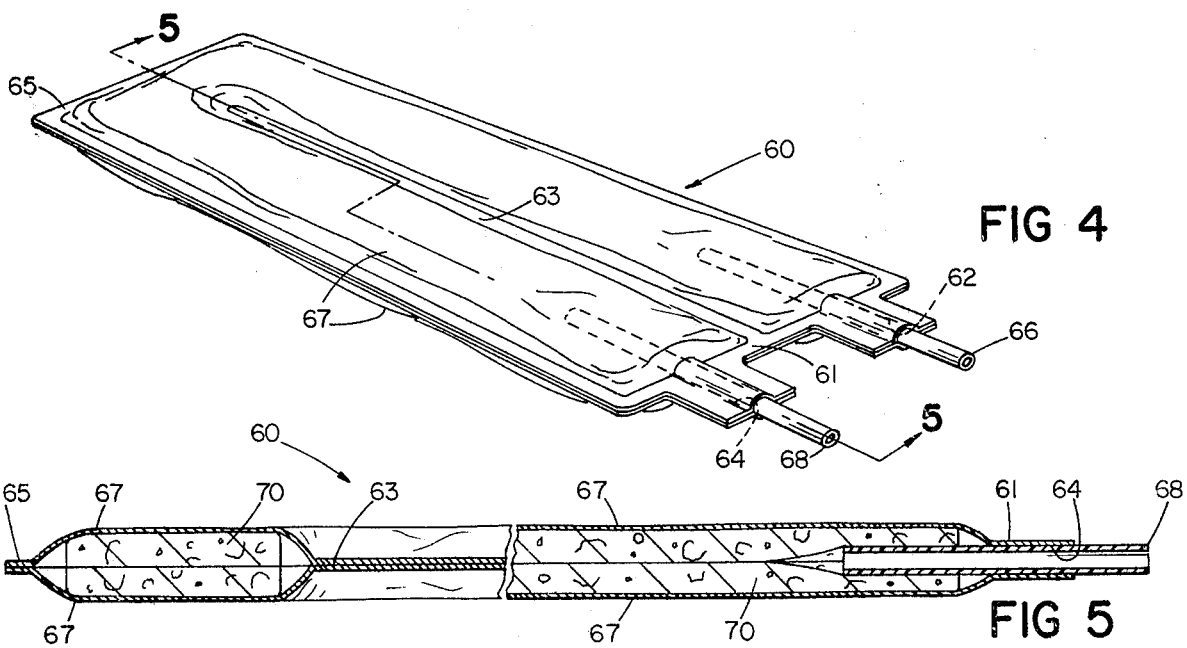
FIG 4
FIG 5

COOLING PAD

FIELD OF THE INVENTION

This invention relates to a cooling pad used to reduce organ metabolism, particularly during cardiac surgery to reduce heart metabolism.

BACKGROUND OF THE INVENTION

In cardiac surgery, the heart is often deprived of blood for a period of time. When this occurs, the heart's energy requirements must be reduced to prevent heart damage. In the prior art two methods are generally used to accomplish this metabolism reduction or myocardial preservation.

One prior art method consists of an initial infusion of a cardioplegic solution into the coronary arteries followed by continued low-flow infusion or intermittent higher-flow infusion. The first infusion initially cools and arrests the heart while the subsequent low-flow infusion or higher-flow infusion maintains the low temperature. The major drawback of this method is that the cardioplegic solution enters the patient's bloodstream thereby diluting the blood with a drug that tends to stop heart action.

Another prior art method, which is sometimes combined with the previously described one, is an external lavage of the heart with cold normal saline. The major drawback of the topical lavage is that the saline pored over the heart becomes mixed with blood in the patient's chest cavity thereby diluting it. Further, the lavage also has an undesirable tendency to cool the surgeon's fingers.

It is also known that organs can be cooled or heated by placing a pad near them, and passing hot or cold fluid through the pad. Shioshvili U.S. Pat. No. 3,738,372 shows an elastic cooling pad which conforms to a kidney and is used to cool it when it is cut off from blood supply. The pad walls, however, are only separated by the fluid in the pad which is under positive pressure. Miley U.S. Pat. No. 3,888,259 shows a standard hypothermia pad which is designed to wrap or otherwise contact a patient. This pad is connected by a return line to a fluid pump, but it does not conform to the patient's body because of negative pressure. Further, fluid only flows through tubing in the pad, the walls of which are not otherwise separated.

SUMMARY OF THE INVENTION

I have discovered that low organ metabolism can be maintained by placing a cooling pad, which has cold fluid flowing therethrough, under and around an organ. The pad comprises flexible walls sealed together at their edges except at an inlet and an outlet which are disposed away from each other. The pad encloses a filler which is flexible and porous and which separates its walls.

In a preferred embodiment the cooling pad is rectangular having an inlet and an outlet at opposite ends of the same long side; inlet and outlet each have tubes sealed therein, and the tubes are connected respectively to an upstream heat exchanger which is lower than the pad and a downstream pump, either causing negative pressure in the pad, all part of a closed fluid loop; the pad encloses a flexible and porous foam filler which separates pad walls of PVC sheet. The walls are heat sealed together at their edges except at the inlet and the outlet.

In another preferred embodiment a rectangular pad is partially divided by a central seal so as to form a U-shaped passage therethrough from an inlet to an outlet.

The invention reduces organ metabolism when the pad is placed underneath the patient's organ and isotonic fluid is pumped therethrough. The flexible pad can be molded around the organ, and it will retain its molded shape because of the negative pressure therein. This increases the cooling effect. The negative pressure also helps to prevent leakage from the pad should it be punctured during operation.

PREFERRED EMBODIMENTS

I turn now to description of the structure and operation of preferred embodiments of the invention, after first briefly describing the drawings.

Drawings

FIG. 1 is a diagrammatic view of a heart cooling system embodying this invention.

FIG. 2 is an enlarged perspective view of a cooling pad of this invention with a portion broken away.

FIG. 3 is a sectional view taken through 3—3 of FIG. 2.

FIG. 4 is an enlarged perspective view of another cooling pad of this invention.

FIG. 5 is a sectional view taken through 5—5 of FIG. 4.

DESCRIPTION

Turning to FIG. 1, there is shown a heart cooling system 100 generally comprising a cooling pad 10, a pump 30, and a heat exchanger 40, all interconnected by tubing to form a closed fluid loop. During open-heart surgery, pad 10 is positioned under and partially surrounds patient's heart 11, while heat exchanger 40 is located below heart and pad level. As shown by the flow direction arrows, pump 30 is downstream from pad 10.

In the most preferred embodiment, as shown in FIGS. 2 and 3, cooling pad 10 is generally rectangular and has an inlet 12 and an outlet 14 extending through opposite ends of one of the long sides of the pad. Pad 10, which has overall dimensions of about 9 inches by 3.5 inches, has walls 16 made of flexible, blood bag grade PVC sheet having a thickness of 0.015 inches. The sheet is embossed on its inner surface. Pad 10 encloses a foam filler 18 of 10 PPI polyester-urethane. Filler 18 separates the sheet walls of pad 10 but is flexible and porous. The edges of pad walls 16 are heat sealed together except at inlet 12 and outlet 14. The heat seal is made so as to avoid entrapping any air or foam filler, and the edge is free of any burrs.

Inlet tube 20 and outlet tube 22 partially extend into pad 10 through respective openings 12, 14 and are sealed in place. Tubes 20, 22 are standard PVC tubes such as Norton Tygon S-50HL or Sunlight 966-9. Tubes 20, 22 have a 0.209 inch outer diameter and a 0.125 inch inner diameter. The portion of tubes 20, 22 outside pad 10 are adapted for connection to other flexible tubing. Pad 10 may have an insulating blanket 24 on its underside. The blanket 24 may be made of closed cell foam.

Pump 30 is a constant flow type such as a blood pump from the Cobe Centry ® 2 Dialysis Delivery Machine. A Sarns 6002 roller pump is also suitable. Pump 30 has a silicone header (not shown) which resists hardening caused by low fluid temperature in the system. Pump 30 has an inlet 32 and an outlet 34. Pump inlet 32 is connected by tubing 36 to the outlet tube 22 of pad 10. Pump outlet 34 is connected (as hereafter described) by additional tubing 38 to heat exchanger 40.

Heat exhanger 40 comprises a reservoir 42, which is a Thermos "Jugler" ™ multi-purpose cooler. Reservoir 42, which may be bracketed to pump 30, holds an ice water bath. A saline bag 46, which is a standard I.V. bag, is wholly or partially immersed in the ice bath. Bag 46 has a pair of ports 50, 52 at one end, and bag 46 is disposed in the reservoir 42 so that ports 50, 52 are adjacent to the reservoir bottom. The end of tubing 38 opposite pump 30 is connected to first port 50. A portion of the tubing 38 connecting pump outlet 34 and bag port 50 is wrapped to form a cooling coil 48 which is also immersed in the bath. Second port 52 is connected by tubing 54 to the inlet tube 20 of pad 10. The tubing 36, 38, 54 is all standard PVC tubing.

OPERATION

First, pad 10, pump 30, and saline bag 46 are all connected by tubing 36, 38, 54. Saline bag 46 and cooling coil 48 are then immersed in the ice bath of heat exchanger reservoir 42, which is positioned lower than the patient's heart.

Pump 30 is activated, and air is bled from the system, which is then filled with normal saline solution or other isotonic liquid. The flow, at a rate of 300 to 400 mil/min., is in the direction indicated by the arrows in FIG. 1.

During open-heart surgery the aorta, which supplies blood to the heart, is cross-clamped cutting off the flow of blood. Heart metabolism is then initially reduced by an infusion or "bolus" injection of a cardioplegic solution into the coronary arteries. This solution arrests the heart action and initially cools it. The reduced metabolism is maintained by slipping pad 10, with the cooled saline solution being pumped therethrough, underneath the heart. Because of the size and shape of the pad 10, it is not necessary to remove the heart to put it in place. Pad 10 is longitudinally positioned under the heart so that the insulation pad 24 is away from the heart. The weight of the heart tends to collapse the pad and wrap it around the heart. The outside surface of pad 10 is sterile, and it has an internal temperature of about 8° C.

There is a negative pressure in the pad when the system is in operation. The negative pressure independently results from positioning heat exchanger 40 below the pad and heart level and also from positioning the pump 30 downstream from the pad. When it is in place, pad 10 is molded around the heart. Surface area contact with the heart is not essential, however. Because of the negative pressure, the pad, which would otherwise flex back to its initial flat shape, retains its molded shape around the heart. The negative pressure also prevents leakage from the pad should it be accidentally punctured. During operation, the pressure inside the pad is approximately 50 mm Hg.

OTHER EMBODIMENTS

In another preferred embodiment shown in FIGS. 4, 5 a cooling pad 60 is rectangular and partially divided by a central heat seal 63, extending from the middle of an edge 61 on one short side along pad's longitudinal axis almost to an opposite edge 65. This creates a U-shaped passage inside the pad. Pad 60 has inlet 62 and outlet 64 in the edge 61 on opposite sides of the central heat seal 63. Inlet tube 66 and outlet tube 68 extend into the pad 60 through the inlet 62 and outlet 64 respectively. Tubes 66, 68 are sealed in place. Flexible and porous foam filler 70 is inside the pads and separates pad walls 67. Of course, pads of other shapes and sizes are also within the scope of this invention.

It is also within the scope of this invention to use the pad to cool organs other than the heart.

What is claimed is:

1. An apparatus for cooling a body organ such as a heart, said apparatus including a cooling pad for surrounding said body organ and a pump for circulating a cooling liquid through said pad, the improvement wherein said pump is arranged with respect to said pad so as to place the liquid inside said pad under negative pressure, and said cooling pad comprises,
an upper flexible sheet,
a lower flexible sheet,
said sheets having an areawise extent suitable for partially surrounding said organ,
said sheets being suited for contact with said body organ and with body fluids, and
said sheet being liquid impermeable and sealed at their peripheral edges to form a bag,
an inlet tube means sealed to said bag for transferring cooling liquid under negative pressure into said bag,
an outlet tube means sealed to said bag at a location spaced from said inlet tube means for transferring said liquid from said bag.
porous and flexible filler element filling the inside of said bag in the space between said upper and lower sheets,
the locations of said tube means together with said sheets defining a flow path for said liquid through the interior of said bag, said flow path being through pores in said porous element and being unconfined by any tube between said inlet tubes means and said outlet tube means,
said porous element being selected to maintain separation between said sheets, and thereby maintain said flow path, when the walls of said bag are squeezed toward each other as the result of said bag being filled with said liquid under negative pressure and being conformed around said organ, and
said porous element, the material from which said sheets are made, and the dimensions of said sheets being selected to permit said bag to retain its shape surrounding said organ when filled with said liquid under negative pressure.

2. The cooling pad of claim 1 wherein a heat exchanger is connected to said pad, said heat exchanger being disposed below the level of said pad.

3. The cooling pad of claim 1 wherein said porous element consists of 10 PPI polyester-urethane foam.

4. The cooling pad of claim 1 wherein said circulating cooling liquid consists of an isotonic fluid.

5. The cooling pad of claim 1 wherein said sheets are made of blood bag grade PVC sheet.

6. The cooling pad of claim 1 wherein said pad is rectangular and said inlet and said outlet are at opposite ends of the same long side.

7. The cooling pad of claim 1 wherein said pad is rectangular and has a central seal extending from the middle of a short side along a major portion of its longitudinal axis.

8. The cooling pad of claim 7 wherein said inlet and said outlet are disposed on said short side and separated by said seal.

* * * * *

UNITED STATES PATENT AND TRADEMARK OFFICE
CERTIFICATE OF CORRECTION

PATENT NO. : 4,259,961

DATED : April 7, 1981

INVENTOR(S) : Andrew G. Hood, III

It is certified that error appears in the above-identified patent and that said Letters Patent are hereby corrected as shown below:

Column 4, line 22, "sheet" should be --sheets--.

Column 4, line 37, "tubes" should be --tube--.

On first page, the assignment should be indicated as follows: --Assignee: Cobe Laboratories, Inc., Lakewood, Colo.--.

Signed and Sealed this

Twenty-fifth Day of August 1981

[SEAL]

Attest:

Attesting Officer

GERALD J. MOSSINGHOFF

Commissioner of Patents and Trademarks